United States Patent
Shi et al.

(10) Patent No.: US 10,471,122 B2
(45) Date of Patent: Nov. 12, 2019

(54) COMPOSITION FOR USE IN PROMOTING WOUND HEALING

(71) Applicant: Blue Blood Biotech Corp., Taipei (TW)

(72) Inventors: Guey-Yueh Shi, Tainan (TW); Kuan-Chieh Wang, Tainan (TW); Yi-Kai Hong, Tainan (TW); Chih-Yuan Ma, Tainan (TW); Hua-Lin Wu, Tainan (TW)

(73) Assignee: Blue Blood Biotech Corp., Taipei (TW)

( * ) Notice: Subject to any disclaimer, the term of this patent is extended or adjusted under 35 U.S.C. 154(b) by 0 days.

(21) Appl. No.: 15/742,501

(22) PCT Filed: Jul. 26, 2016

(86) PCT No.: PCT/US2016/044086
§ 371 (c)(1),
(2) Date: Jan. 6, 2018

(87) PCT Pub. No.: WO2017/023623
PCT Pub. Date: Feb. 9, 2017

(65) Prior Publication Data
US 2018/0200329 A1    Jul. 19, 2018

Related U.S. Application Data

(60) Provisional application No. 62/199,676, filed on Jul. 31, 2015.

(51) Int. Cl.
| | | |
|---|---|---|
| A61K 38/00 | (2006.01) | |
| C07K 14/705 | (2006.01) | |
| A61K 38/16 | (2006.01) | |
| A61P 17/02 | (2006.01) | |
| A61K 9/00 | (2006.01) | |
| A61L 15/44 | (2006.01) | |
| A61L 27/54 | (2006.01) | |

(52) U.S. Cl.
CPC ............ *A61K 38/16* (2013.01); *A61K 9/0014* (2013.01); *A61L 15/44* (2013.01); *A61L 27/54* (2013.01); *A61P 17/02* (2018.01)

(58) Field of Classification Search
None
See application file for complete search history.

(56) References Cited

U.S. PATENT DOCUMENTS

2005/0142138 A1 * 6/2005 St. Croix .............. C07K 16/30
424/155.1

FOREIGN PATENT DOCUMENTS

WO    WO-2004078192 A1 * 9/2004 ......... A61K 38/1709

OTHER PUBLICATIONS

Tokuriki et al. Stability effects of mutations and protein evolvability; Current Opinion in Structural Biology, 19:596-604 (2009). (Year: 2009).*
Bhattacharya et al. Impact of genetic variation on three dimensional structure and function of proteins; PLOS One 12(3): e0171355, pp. 1-22 (Mar. 2017). (Year: 2017).*
Babu et al "TGFβ-mediated suppression of CD248 in non-cancer cells via canonical Smad-dependent signaling pathways is uncoupled in cancer cells" BMC Cancer 2014, 14:113.
International Search Report for PCT/US16/044086, dated Oct. 21, 2016.
Written Opinion of the International Searching Authority for PCT/US16/044086, dated Oct. 21, 2016.
National Digital Library of Theses an Dissertations in Taiwan, [online] [retrieved on Jan. 5, 2018] Retrieved from the internet: https://ndltd.ncl.edu.tw/cgi-bin/gs32/gsweb.cgi/ccd=0XjjXA/record?r1=2&h1=1 "Study of Endosialin in Cancer Associated Fibroblast-mediated Angiogenesis", deposited in university library indexed, cataloged and shelved on Oct. 3, 2012.

* cited by examiner

*Primary Examiner* — Joanne Hama
*Assistant Examiner* — Regina M DeBerry
(74) *Attorney, Agent, or Firm* — Hsiu-Ming Saunders; Intellectual Property Connections, Inc.

(57) ABSTRACT

A pharmaceutical composition for use in promoting wound healing and/or accelerating closure of an open wound in a subject in need thereof is disclosed. The composition comprises a therapeutically effective amount of a recombinant polypeptide comprising an amino acid sequence that is at least 80% identical to the amino acid sequence of SEQ ID NO: 2; and a pharmaceutically acceptable vehicle, carrier, diluent, excipients, and/or salt.

6 Claims, 7 Drawing Sheets
Specification includes a Sequence Listing.

COMPOSITION FOR USE IN PROMOTING WOUND HEALING

REFERENCE TO RELATED APPLICATION

This application is a national stage application (under 35 U.S.C. 371) of PCT/US2016/044086 filed on 26 Jul. 2016, which claims priority to U.S. provisional application 62/199,676 filed on 31 Jul. 2015, all of which are herein incorporated by reference in their entireties.

FIELD OF THE INVENTION

The present invention relates generally to wound healing, and more specifically to compositions for use in promoting wound healing.

BACKGROUND OF THE INVENTION

Diabetes is one of the serious global issues. Approximately 285 million people are affected by diabetes worldwide. Up to 25% of diabetic patients develop diabetic foot ulcers that lead to poor quality of life and the risk of lower-extremity amputation. The current methods for clinical treatment of diabetic wounds including glycemic control, debridement, removing infectious agents, moisture dressings, and offloading high pressure from wounds may facilitate would closure, but there is no efficient treatment strategy for all patients with diabetic wounds. Some patients failed to heal using these standard approaches. This indicates that the fundamental and molecular events of impaired wound healing are in need for further investigations.

Wound healing is a complicated biological process that can be divided into four overlapping phases: hemostasis, inflammation, proliferation, and tissue remodeling. In hemostasis phase, platelets aggregate and quickly trigger fibrin clot formation that can protect wounds and prevent bacterial invasion after cutaneous wound injury. Inflammatory phase begins within 2-3 days. Leukocytes, such as neutrophils and macrophages, are attracted to wound lesions by chemokines secreted from injured tissues. Recruitment of leukocytes also participates in clearance of invasive pathogens and induction of inflammatory response by production of inflammatory cytokines. The process of neovascularization concurrently occurs with the proliferation of fibroblasts and keratinocytes and the deposition of extracellular matrix in proliferation phase. Finally, several events occur in tissue remodeling phase, including the appearance of myofibroblasts, extracellular matrix remodeling, and scar formation.

Tumor endothelial marker 1 (TEM1), also known as endosialin or CD248, is initially identified as a highly up-regulated protein in tumor vasculature. TEM1 consists of six domains, including an N-terminal lectin-like domain (TEM1 domain 1. TEM1 D1), a sushi-like domain (TEM1D2), a three-repeated epidermal growth factor (EGF)-like domain (TEM1D3), a mucin-like domain (TEM1D4), a transmembrane domain (TEM1D5), and a cytoplasmic domain (TEM1D6). Recent reports have shown that TEM1 knockout mice exhibited a reduction in tumor growth, invasiveness and metastasis of colorectal xenografts compared with wild type mice. It has also been demonstrated that TEM1 facilitates tumor growth and inflammatory arthritis via its cytoplasmic domain. These results suggest that TEM1 plays a role in physiological and pathological conditions.

SUMMARY OF THE INVENTION

In one aspect, the invention relates to use of a composition comprising: (a) a therapeutically effective amount of a recombinant polypeptide comprising an amino acid sequence that is at least 80% identical to the amino acid sequence of SEQ ID NO: 2; and (b) a pharmaceutically acceptable vehicle, carrier, diluent, excipients, and/or salt, in the manufacture of a medicament for promoting wound healing and/or accelerating closure of an open wound in a subject in need thereof.

Alternatively, the invention relates to a pharmaceutical composition comprising: (a) a therapeutically effective amount of a recombinant polypeptide comprising an amino acid sequence that is at least 80% identical to the amino acid sequence of SEQ ID NO: 2; and (b) a pharmaceutically acceptable vehicle, carrier, diluent, excipients, and/or salt, for use in promoting wound healing and/or accelerating closure of an open wound in a subject in need thereof.

The invention also relates to a method of promoting wound healing and/or accelerating closure of an open wound in a subject in need thereof, comprising: administering to the subject in need thereof a composition comprising: (a) a therapeutically effective amount of a recombinant polypeptide comprising an amino acid sequence that is at least 80% identical to the amino acid sequence of SEQ ID NO: 2; and (b) a pharmaceutically acceptable vehicle, carrier, diluent, excipients, and/or salt.

In one embodiment of the invention, the recombinant polypeptide comprises domains 2 and 3, and does not comprise domains 1, 4, 5, and 6 of tumor endothelial marker 1.

In another embodiment of the invention, the recombinant polypeptide comprises domain 3, and does not comprise domains 1, 2, and 4 to 6 of tumor endothelial marker 1.

In another embodiment, the recombinant polypeptide comprises domains 1 to 4 and does not comprise domains 5 and 6 of tumor endothelial marker 1.

In another embodiment, the recombinant polypeptide comprises domains 2 to 4, and does not comprise domains 1, 5, and 6 of tumor endothelial marker 1.

In another embodiment, the recombinant polypeptide comprises domains 3 and 4 and does not comprise domains 1, 2, 5, and 6 of tumor endothelial marker 1.

In another embodiment, the recombinant polypeptide comprises an amino acid sequence that is at least 90% identical to the amino acid sequence of SEQ ID NO: 2.

In another embodiment, the recombinant polypeptide comprises the amino acid sequence of SEQ ID NO: 2.

In another embodiment, the recombinant polypeptide comprises the amino acid sequence of SEQ ID NO: 4.

Further in another embodiment, the recombinant polypeptide is encoded by a DNA comprising the nucleotide sequence of SEQ ID NO: 1.

In another embodiment, the medicament is in a dosage form that is selected from the group consisting of gel, cream, paste, lotion, spray, suspension, solution, dispersion salve, hydrogel, and ointment.

In another embodiment, the wound is at least one selected from the group consisting of diabetic foot ulcer, surgical wound, incision, laceration, abrasion, puncture wound, and crushing injury, or wherein the wound results from dermabrasion, first-degree burn, second-degree burn, third-degree burn, chemical burn, or laser resurfacing.

In another embodiment, the wound extends to the subcutaneous tissue panniculus carnosus.

In another embodiment, the subject is a diabetic.

Further in another embodiment, the subject suffers from a diabetic foot ulcer.

In another embodiment of the invention, the recombinant polypeptide comprises no more than 130 amino acid residues.

In another embodiment of the invention, the recombinant polypeptide consists of the amino acid sequence of SEQ ID NO: 2.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a". "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of a therapeutic agent to a subject in need thereof. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on route of administration, excipient usage, and the possibility of co-usage with other therapeutic treatment.

The "Guidance for Industry and Reviewers Estimating the Safe Starting dose in Clinical Trials for Therapeutics in Adult Healthy Volunteers" published by the U.S. Department of Health and Human Services Food and Drug Administration discloses "a human equivalent dose" may be obtained by calculations from the following formula:

HED=animal dose in mg/kg×(animal weight in kg/human weight in kg)$^{0.33}$.

As used herein, when a number or a range is recited, ordinary skill in the art understand it intends to encompass an appropriate, reasonable range for the particular field related to the invention.

By about 0.2-1000 mg it meant that all tenth and integer unit amounts within the range are specifically disclosed as part of the invention. Thus, 0.2, 0.3, 0.4 and 1, 2, 3, 4 . . . 999.7, 999.8, 999.9 and 1000 unit amounts are included as embodiments of this invention.

For topical use, the dosage can be calculated depending on the size of the wound opening. Usually one may prepare a solution of drug at a specific concentration and apply a volume of the drug depending on the size of the wound. In the example of a mice model disclosed below, the dosage is 0.2 mg/Kg, which is equal to 5 μg per mouse, and is equal to 10 μg/cm$^2$ of the wound area. The wound was of about 0.5 cm$^2$. Thus, in one embodiment, the dosage ranges from 0.1 μg/cm$^2$ to 100 mg/cm$^2$ of a wound area.

TEM1 (SEQ ID NO: 3; full-length) stands for tumor endothelial marker 1.

TEM1D3 (SEQ ID NO: 2) stands for TEM1 domain 3. TEM1D3-encoding DNA sequence is SEQ ID NO: 1. The invention relates to the discovery that recombinant TEM1 D3 (rTEM1D3) alone functions as an angiogenic factor and can promote skin wound healing.

TEM1 D1-4 (SEQ ID NO: 4) stands for TEM1 domain 1 to domain 4.

Methods and Materials

Preparation of rTEM1D1-4 and rTEM1D3.

To prepare rTEM1D1-4, which is consisted of lectin-like domain, Sushi domain, EOF-like repeats and mucin-like region, the pSecTaq2-A vector (Invitrogen) containing aforementioned domains of human TEM1 was used for the expression and secretion of rTEM1D1-4 in an embryonic kidney HEK293 protein expression system. rTEM1D1-4 was purified from the conditioned medium using a nickel-chelating Sepharose column (Amersham Pharmacia Biotech). The purity of rTEM1D1-4 was evaluated by Coomassie blue staining and Western blotting. The rTEM1D1-4 is composed of a polypeptide Trp$^{21}$-Gln$^{681}$ of SEQ ID NO: 3). To prepare rTEM1D3, EGF-like domain of TEM1 gene was constructed into the pPICZα-A vector (Invitrogen). The constructed vector was transfected into Pichia pastoris, and recombinant rTEM1D3 was purified from the fermented medium. The purity of rTEM1D3 was evaluated by Coomassie blue staining and Western blotting. The rTEM1D3 is composed of a polypeptide (Cys$^{235}$-Cys$^{350}$ of SEQ ID NO: 3).

Endothelial Cell Proliferation, Migration, and Tube Formation.

To assess the ability of rTEM1D1-4 or rTEM1D3 to stimulate human umbilical vein endothelial cells (HUVECs) proliferation, tetrazolium salt WST-1 (4-[3-(4-iodophenyl)-2-(4-nitrophenyl)-2H-5-tetrazolio]-1,3-benzene disulfonate) was used in accordance with the manufacturer's instruction (Roche). HUVECs were treated with different concentrations of rTEM1D1-4 or rTEM1D3 for 48 h. WST-1 was added to each well, and the absorbance was measured at a wavelength of 450 nm. HUVECs migration was measured using Transwell (Corning Costar Corp.) with 6.5-mm-diameter polycarbonate filters (8-μM pore size). Different concentrations of rTEM1D1-4 or rTEM1D3 were placed in the lower wells. HUVECs were seeded into each upper well at a density of 1×10$^5$ in M199 medium containing 1% FBS and were allowed to migrate for 4 h at 37° C. The cells were stained by Liu's stain. The total migrated cells were counted under an optical microscope (Olympus). To assay tube formation ability, HUVECs were resuspended at a density of 1×10$^5$/ml in M199 containing 4% FBS. Cell suspensions treated with various concentrations of rTEM1D1-4 or rTEM1D3 were added to wells of μ-slide Angiogenesis (Integrated BioDiagnostics), which contained growth factor-reduced Matrigel (BD Biosciences). Capillary-like structures were photographed with Olympus microscope. rTEM1D3 was inactivated by heating in the presence of 2-mercaptoenthnol.

Cutaneous Wound Healing Assay.

C57BL/6 male mice (8-12 weeks of age; body weight 25±2 g) were created a 7-mm diameter dorsal wound at day 0. Ten microliters of PBS or rTEM1D3 dissolved in PBS (0.2 mg/kg/mouse) was applied directly to wound area once daily from day 1 to day 7 for 7 consecutive days. Wound closure rate was analyzed at day 1, 3, 5, and 7.

Immunofluorescence Stain to Measure Angiogenesis in the Wound.

C57BL/6 male mice (8-12 weeks of age) were created a 7-mm diameter dorsal wound at day 0. Ten μl of PBS or rTEM1D3 (0.2 mg/kg/mouse) was applied directly to wound area once daily for another 4 consecutive days. Skin wound sections were obtained from mice treated with PBS or rTEM1D3. CD31 staining was performed by rat anti-mouse CD31 antibody (BD Bioscience), and fluorescence intensity of CD31 in granulation tissue of wounds was analyzed using the Image J software.

Keratinocyte Proliferation and Migration.

The effect of rTEM1D1-4 on proliferation activity of HaCaT was detected by using tetrazolium salt WST-1 (4-[3-(4-iodophenyl)-2-(4-nitrophenyl)-2H-5-tetrazolio]-1,3-benzene disulfonate) with the manufacturer's instruction (Roche). HaCaT cells were treated with different concentrations of rTEM1D1-4 for 48 h. WST-1 was added to each well, and the absorbance was measured at a wavelength of 450 nm. The migration ability of HaCaT cells was evaluated by transwell system (8-μM pore size) that HaCaT cells were seeded in the upper chamber and attracted to rTEM1D1-4 containing lower chamber. HaCaT cells were seeded into each upper well at a density of 5×10⁴ in DMEM medium containing 5% FBS and were allowed to migrate for 16 h at 37° C. The cells were stained by Liu's stain. The total migrated cells were counted under an optical microscope (Olympus).

Statistical Analyses.

Statistical significance was analyzed using one-way ANOVA with a Bonferroni post-test and parametric unpaired t test. Differences between more than two groups were compared using two-way ANOVA with a Bonferroni post-test. Survival data were analyzed using a log-rank test. The P values<0.05 were considered statistically significant.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Figure 1:
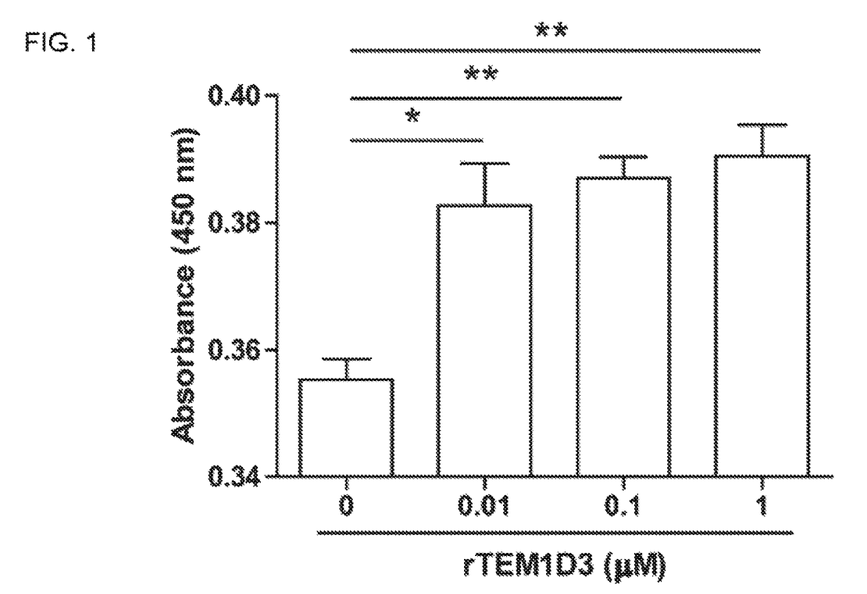
FIG. 1. shows that recombinant TEM1 D3 (rTEM1D3) promotes endothelial cell proliferation. Proliferation of human umbilical vein endothelial cells (HUVECs) was significantly increased with rTEM1D3 stimulation. Data shown are mean±SEM (n=3). *P<0.05, **P<0.01, one-way ANOVA with a Bonferroni posttest.
Figure 2A:
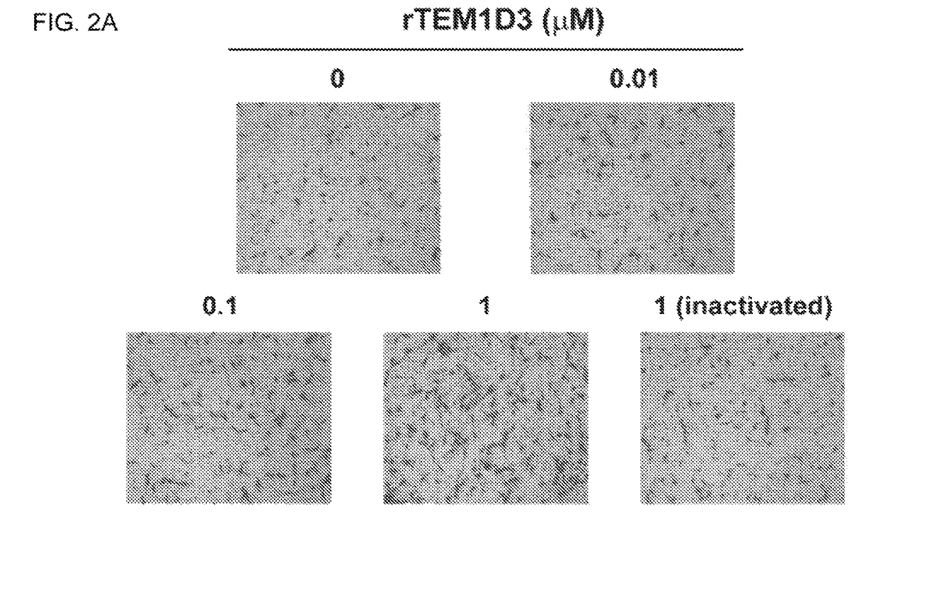
FIGS. 2A-B show that rTEM1D3 promotes endothelial cell migration. (A, B) Migration of HUVECs was significantly increased with rTEM1D3 stimulation. The effect of rTEM1D3 was abolished when rTEM1D3 was heat-inactivated. Data shown are mean f SEM (n=3). ***P<0.001, one-way ANOVA with a Bonferroni posttest.
Figure 2B:
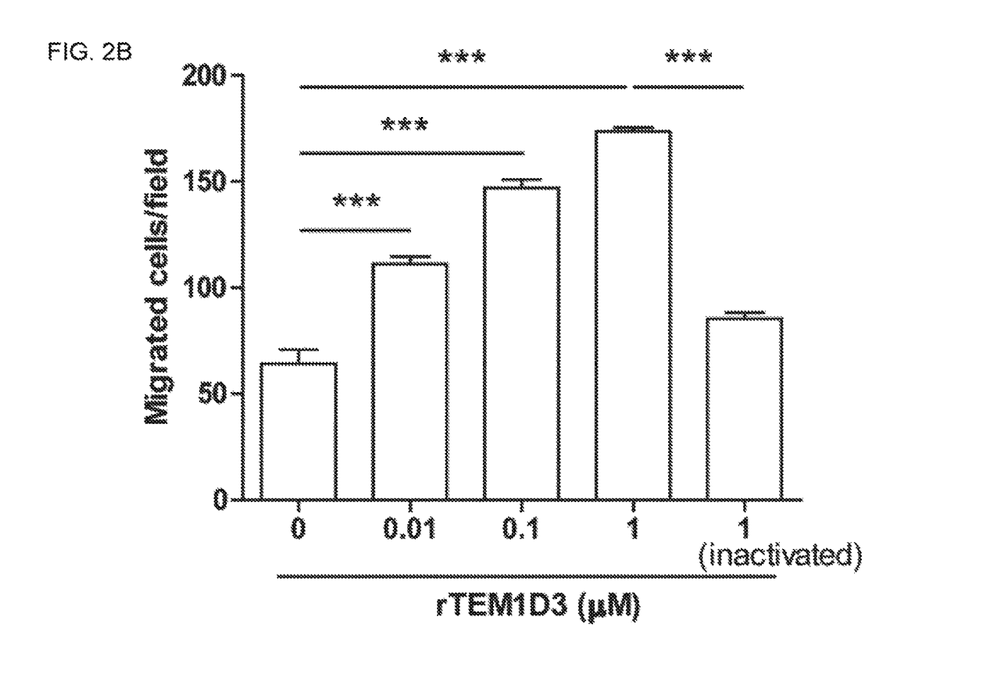
Figure 3A:
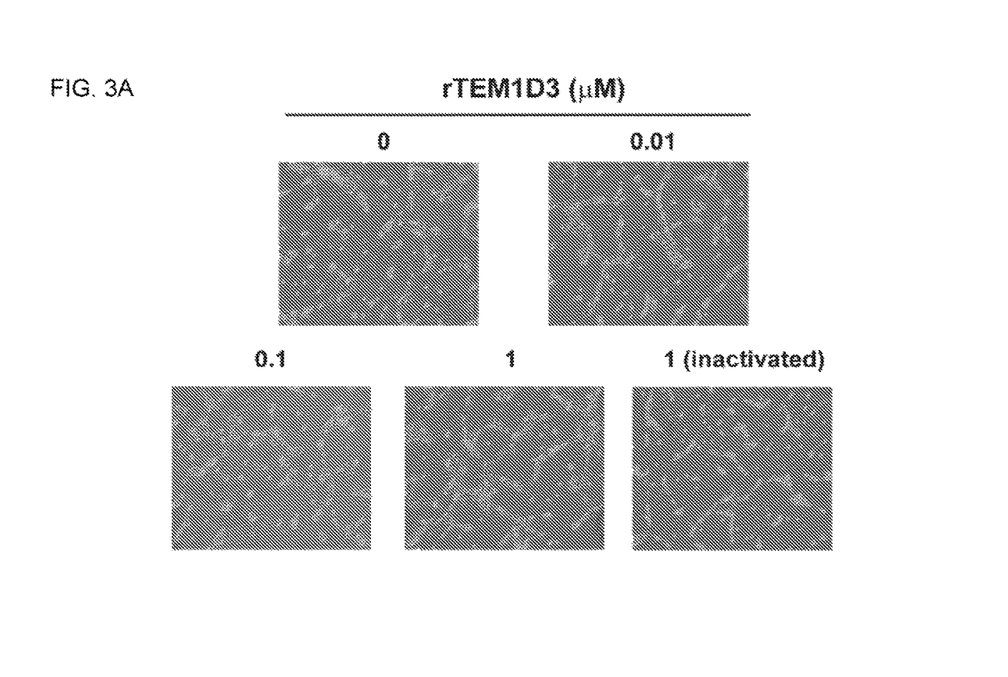
FIGS. 3A-B show that rTEM1D3 promotes endothelial cell tube formation. (A, B) Tube formation of HUVECs was significantly increased with rTEM1D3 stimulation. The effect of rTEM1D3 was abolished when rTEM1D3 was heat-inactivated. Data shown are mean±SEM (n=3). *P<0.05. ***P<0.001, one-way ANOVA with a Bonferroni posttest.
Figure 3B:
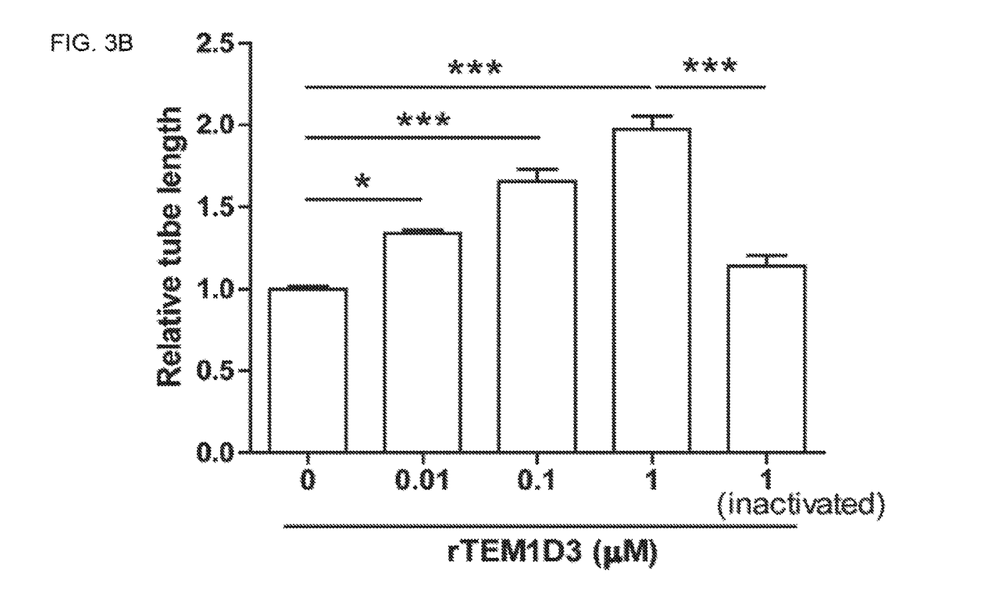
Figure 6:
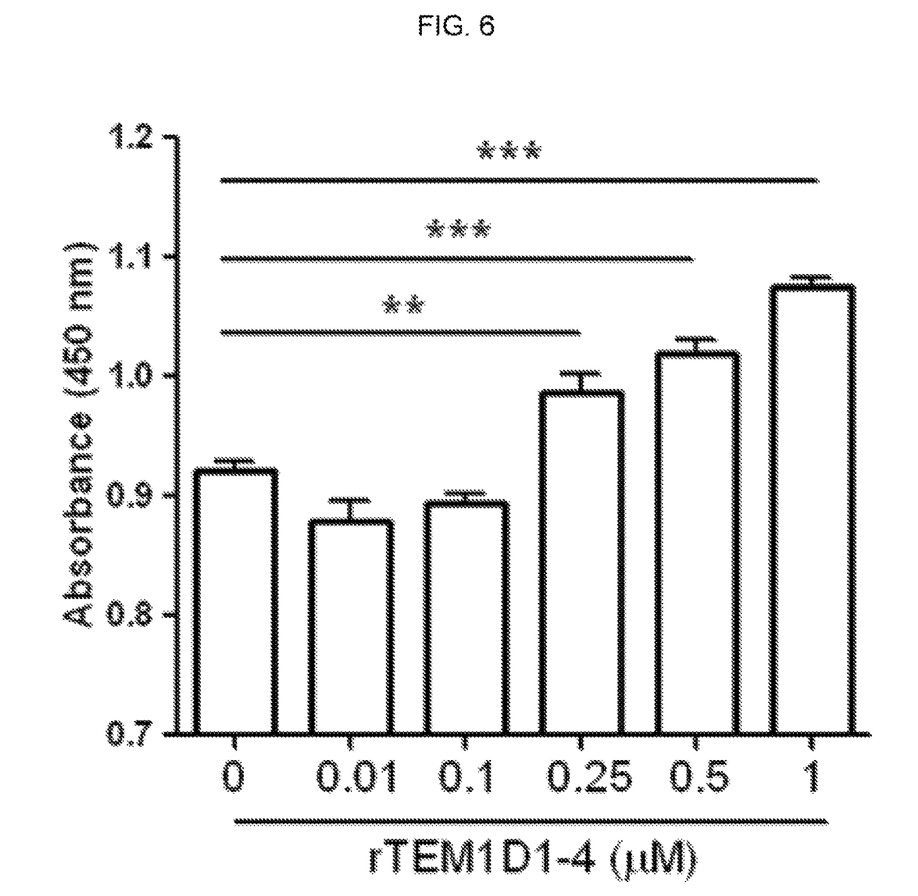
FIG. 6 shows that rTEM1D1-4 promotes endothelial cell proliferation. Proliferation of HUVECs was significantly increased with rTEM1D1-4 stimulation. Data shown are mean±SEM (n=5). P<0.01, * P<0.001 one-way ANOVA with a Bonferroni posttest.
Figure 7A:
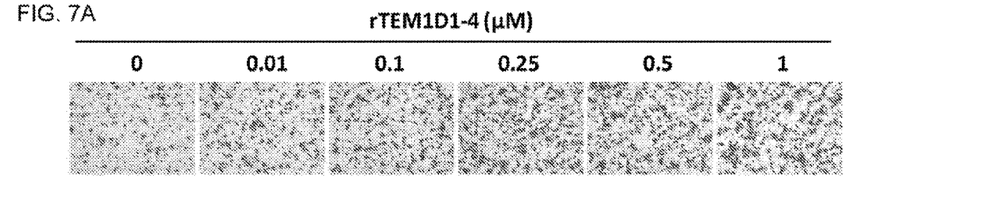
FIGS. 7A-B show that rTEM1D1-4 promotes endothelial cell migration. (A, B) Migration of HUVECs was significantly increased with rTEM1D1-4 stimulation. Data shown are mean±SEM (n=4). *P<0.05, ***P<0.001, one-way ANOVA with a Bonferroni posttest.
Figure 7B:
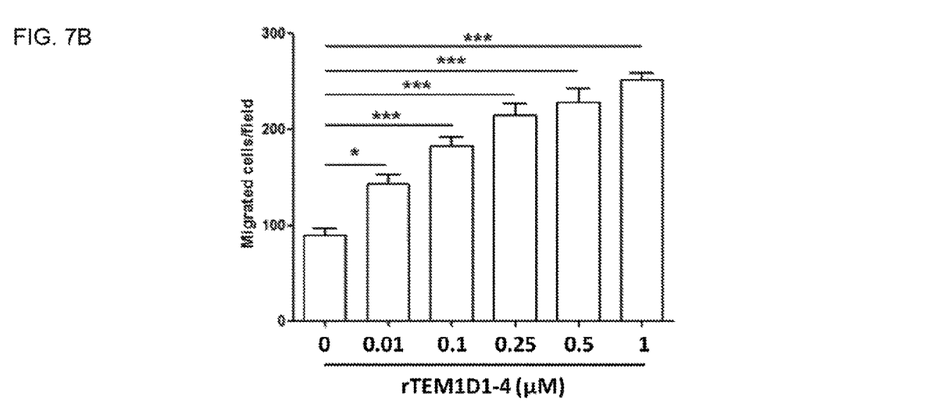
Figure 8A:
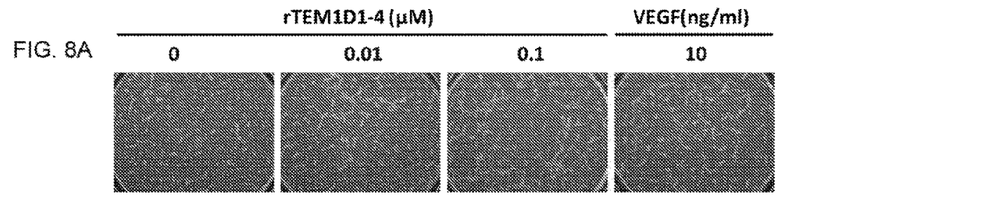
FIGS. 8A-B show that rTEM1D1-4 promotes endothelial cell tube formation. (A, B) Tube formation of HUVECs was significantly increased with rTEM1D1-4 stimulation. Vascular endothelial growth factor (VEGF) was used as positive control. Data shown are mean f SEM (n=3). P<0.01, *P<0.001, one-way ANOVA with a Bonferroni posttest.
Figure 8B:
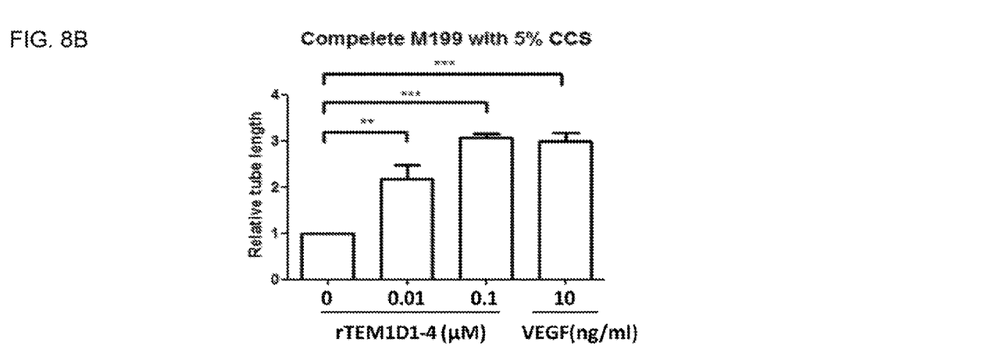

Example 1 rTEM1D1-4 and rTEM1D3 Enhance Endothelial Cell Proliferation, Migration, and Tube Formation The effect of rTEM1D3 and rTEM1D1-4 on the proliferation of HUVECs was respectively evaluated by WST-1 assay. HUVEC proliferation was increased by either rTEM1D3 or rTEM1D1-4 treatment (FIGS. 1 and 6). The chemotactic motility of HUVECs was assayed using Transwell to investigate the effect of rTEM1D1-4 and rTEM1D3 on HUVECs migration. Both rTEM1D3 and rTEM1D1-4 could induce HUVECs migration in a dose-dependent manner (FIGS. 2A-B and 7A-B). Capillary-like structures formed complete networks after 6 h incubation in the presence of different concentrations of rTEM1D3 or rTEM1D1-4, and both rTEM1D3 and rTEM1D1-4 markedly induced a dose-dependent response of tube formation in HUVECs (FIGS. 3A-B and 8A-B).

Example 2 rTEM1D3 Accelerates Skin Wound Closure by Increase of Angiogenesis

Figure 4A:
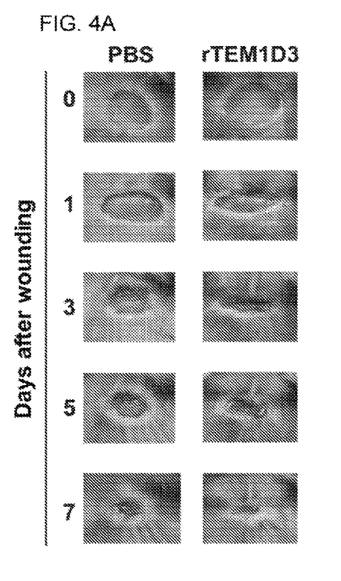
FIGS. 4A-B show that rTEM1D3 significantly improves cutaneous wound healing in mice. (A, B) Wounds (7-mm diameter) were created on wild type C57BL/6 mice, and mice were locally administered with phosphate buffered saline (PBS, n=6) or rTEM1D3 (0.2 mg/kg/mouse, n=8). Wound closure rate was analyzed at day 1, 3, 5, and 7. Data shown are mean±SEM. ***P<0.001, two-way ANOVA with a Bonferrroni posttest, ns, no significance.
Figure 4B:
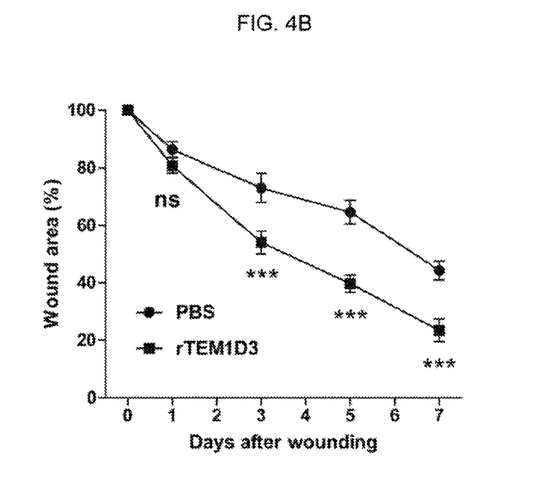
Figure 5A:
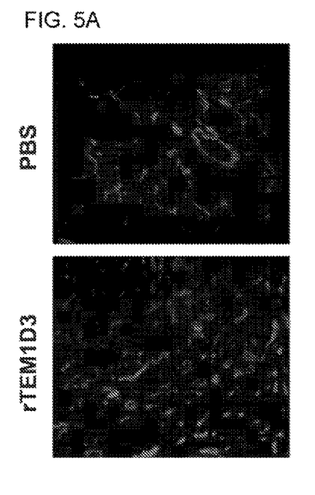
FIGS. 5A-B show that rTEM1D3 treatment increases angiogenesis in wounds of mice. (A, B) Skin wound sections were obtained from wild type C57BL/6 mice treated with PBS (n=6) or rTEM1D3 (0.2 mg/kg/mouse, n=6) for 4 days. CD31 staining was performed, and fluorescence intensity of CD31 in granulation tissue of wounds was analyzed. Data shown are mean±SEM. ***P<0.001, unpaired t test.
Figure 5B:
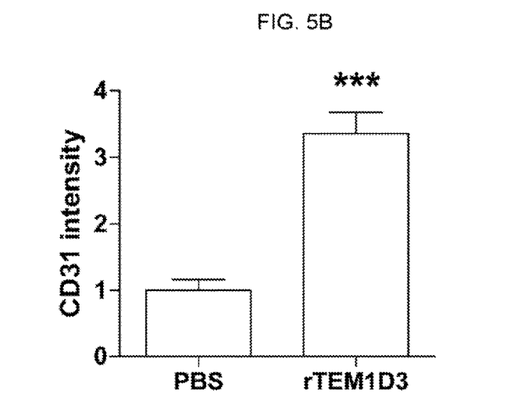

To test whether rTEM1D3 improves skin wound healing in mice, wild type C57BL/6 male mice were caused to have a 7-mm dorsal wound. After 24 h, rTEM1D3 was locally administered to mice for further 7 days, and wound area was recorded. The results showed that wound closure rate was significantly increased after treatment of rTEM1D3 in mice (FIG. 4). Furthermore, angiogenesis was enhanced in the wound area of mice after treatment of rTEM1D3 (FIG. 5). These results suggest that rTEM1D3 can be an angiogenic factor and can also accelerate cutaneous wound healing.

Figure 9:
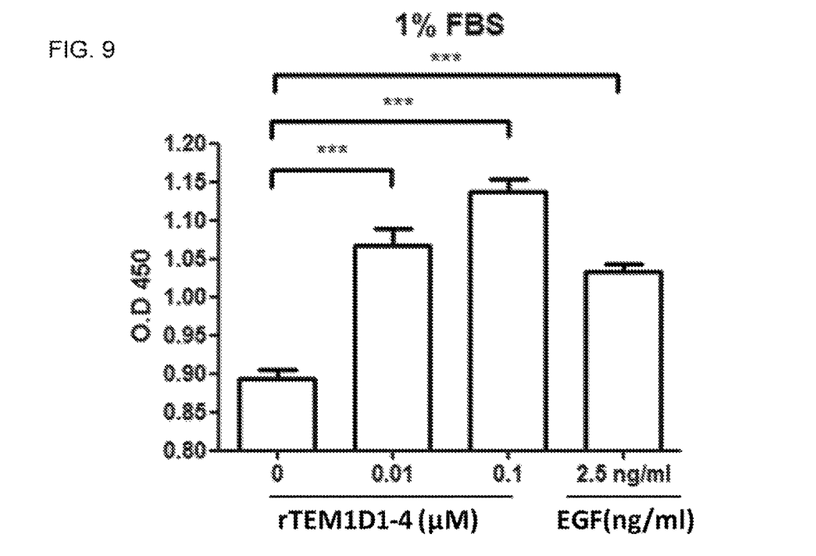
FIG. 9 shows that rTEM1D1-4 stimulates proliferation of human HaCaT cells. Proliferation of HaCaT cells was significantly increased with 1% FBS plus rTEM1D1-4. Epidermal growth factor (EGF) was used as positive control. Data shown are mean f SEM (n=3). ***P<0.001, one-way ANOVA with a Bonferroni posttest.

Example 3 rTEM1D1-4 Effectively Enhances Human Keratinocyte Proliferation and Migration FIG. 9 shows that rTEM1D1-4 stimulates proliferation of human HaCaT cells. Proliferation of HaCaT cells was significantly increased with 1% FBS plus rTEM1D1-4. Epidermal growth factor (EGF) was used as positive control. Data shown are mean±SEM (n=3). ***P<0.001, one-way ANOVA with a Bonferroni posttest.

Figure 10A:
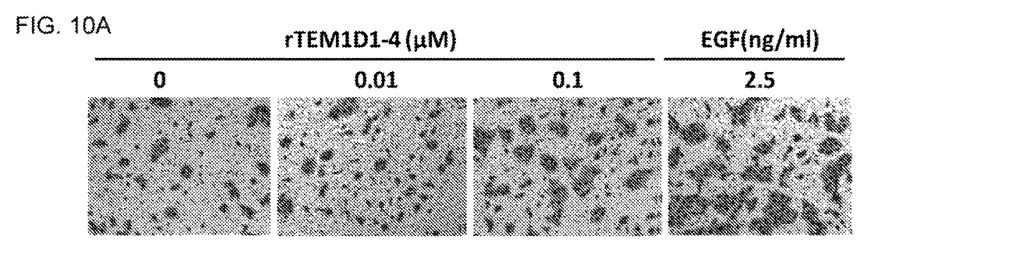
FIG. 10A-B shows that rTEM1D1-4 promotes migration of human HaCaT cells. (A, B) Migration of HaCaT cells was significantly increased with 5% FBS plus rTEM1D1-4. Epidermal growth factor (EGF) was used as positive control. Data shown are mean±SEM (n=3). *P<0.05, ***P<0.001, one-way ANOVA with a Bonferroni posttest.
Figure 10B:
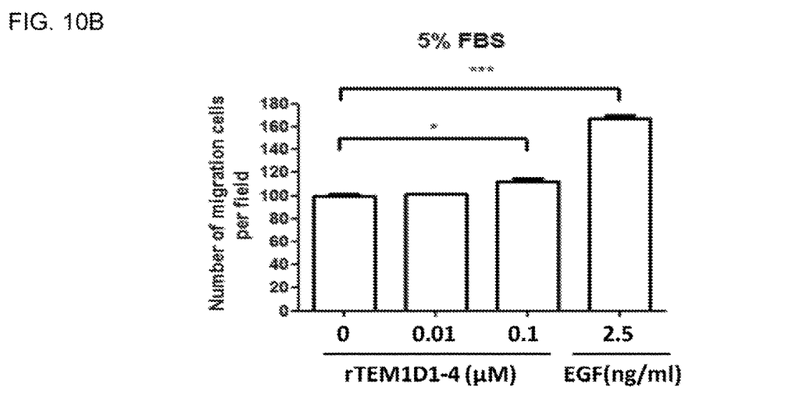

FIG. 10A-B shows that rTEM1D1-4 promotes migration of human HaCaT cells. (A. B) Migration of HaCaT cells was significantly increased with 5% FBS plus rTEM1D1-4. Epidermal growth factor (EGF) was used as positive control. Data shown are mean±SEM (n=3). *P<0.05, ***P<0.001, one-way ANOVA with a Bonferroni posttest.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method for promoting wound healing and/or accelerating closure of an open wound in a subject in need thereof, comprising:
    administering to the subject in need thereof a composition comprising:
    (a) a therapeutically effective amount of a recombinant polypeptide consisting of the amino acid sequence of SEQ ID NO: 2 or SEQ ID NO: 4; and
    (b) a pharmaceutically acceptable vehicle, carrier, diluent, excipients, and/or salt.

2. The method of claim 1, wherein the composition is in a dosage form that is selected from the group consisting of powder, gel, cream, paste, lotion, spray, suspension, solution, dispersion salve, hydrogel, and ointment.

3. The method of claim 1, wherein the wound is at least one selected from the group consisting of diabetic foot ulcer, surgical wound, incision, laceration, abrasion, puncture wound, and crushing injury, or wherein the wound results from dermabrasion, first-degree burn, second-degree burn, third-degree burn, chemical burns or laser resurfacing.

4. The method of claim 1, wherein the subject is a diabetic.

5. The method of claim 1, wherein the wound extends to the subcutaneous tissue pannicalus carnosus.

6. The method of claim 1, wherein the subject suffers from a diabetic foot ulcer.

* * * * *

SEQUENCE LISTING

<160> NUMBER OF SEQ ID NOS: 4

<210> SEQ ID NO 1
<211> LENGTH: 348
<212> TYPE: DNA
<213> ORGANISM: Homo sapiens

<400> SEQUENCE: 1
tgcagccctg acaacggggg ctgcgaacac gaatgtgtgg aggaggtgga tggtcacgtg        60

-continued

```
tcctgccgct gcactgaggg cttccggctg gcagcagacg ggcgcagttg cgaggacccc      120
tgtgcccagg ctccgtgcga gcagcagtgt gagcccggtg ggccacaagg ctacagctgc      180
cactgtcgcc tgggtttccg gccagcggag gatgatccgc accgctgtgt ggacacagat      240
gagtgccaga ttgccggtgt gtgccagcag atgtgtgtca actacgttgg tggcttcgag      300
tgttattgta gcgagggaca tgagctggag gctgatggca tcagctgc                   348
```

```
<210> SEQ ID NO 2
<211> LENGTH: 116
<212> TYPE: PRT
<213> ORGANISM: Homo sapiens

<400> SEQUENCE: 2

Cys Ser Pro Asp Asn Gly Gly Cys Glu His Glu Cys Val Glu Val
1               5                   10                  15

Asp Gly His Val Ser Cys Arg Cys Thr Glu Gly Phe Arg Leu Ala Ala
                20                  25                  30

Asp Gly Arg Ser Cys Glu Asp Pro Cys Ala Gln Ala Pro Cys Glu Gln
            35                  40                  45

Gln Cys Glu Pro Gly Gly Pro Gln Gly Tyr Ser Cys His Cys Arg Leu
        50                  55                  60

Gly Phe Arg Pro Ala Glu Asp Pro His Arg Cys Val Asp Thr Asp
65                  70                  75                  80

Glu Cys Gln Ile Ala Gly Val Cys Gln Gln Met Cys Val Asn Tyr Val
                85                  90                  95

Gly Gly Phe Glu Cys Tyr Cys Ser Glu Gly His Glu Leu Glu Ala Asp
            100                 105                 110

Gly Ile Ser Cys
        115
```

```
<210> SEQ ID NO 3
<211> LENGTH: 757
<212> TYPE: PRT
<213> ORGANISM: Homo sapiens

<400> SEQUENCE: 3

Met Leu Leu Arg Leu Leu Leu Ala Trp Ala Ala Ala Gly Pro Thr Leu
1               5                   10                  15

Gly Gln Asp Pro Trp Ala Ala Glu Pro Arg Ala Ala Cys Gly Pro Ser
                20                  25                  30

Ser Cys Tyr Ala Leu Phe Pro Arg Arg Arg Thr Phe Leu Glu Ala Trp
            35                  40                  45

Arg Ala Cys Arg Glu Leu Gly Gly Asp Leu Ala Thr Pro Arg Thr Pro
        50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
        115                 120                 125

Gln Arg Cys Val Ala Leu Glu Ala Ser Gly Glu His Arg Trp Leu Glu
    130                 135                 140

Gly Ser Cys Thr Leu Ala Val Asp Gly Tyr Leu Cys Gln Phe Gly Phe
145                 150                 155                 160
```

```
Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Val Gly Trp Ser
210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Val Asp Gly His Val Ser Cys
                245                 250                 255

Arg Cys Thr Glu Gly Phe Arg Leu Ala Ala Asp Gly Arg Ser Cys Glu
                260                 265                 270

Asp Pro Cys Ala Gln Ala Pro Cys Glu Gln Gln Cys Glu Pro Gly Gly
            275                 280                 285

Pro Gln Gly Tyr Ser Cys His Cys Arg Leu Gly Phe Arg Pro Ala Glu
        290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
                340                 345                 350

Ala Gly Ala Met Gly Ala Gln Ala Ser Gln Asp Leu Gly Asp Glu Leu
            355                 360                 365

Leu Asp Asp Gly Glu Asp Glu Glu Asp Glu Asp Glu Ala Trp Lys Ala
        370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
        435                 440                 445

Arg Pro Val Val Val Ser Ala Thr His Pro Thr Leu Pro Ser Ala His
450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
                500                 505                 510

Gln Pro Pro Met Ile Ser Thr Lys Tyr Pro Glu Leu Phe Pro Ala His
            515                 520                 525

Gln Ser Pro Met Phe Pro Asp Thr Arg Val Ala Gly Thr Gln Thr Thr
        530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575
```

-continued

```
Thr Gln Ala Thr Gln Leu Pro Ile Ile Pro Thr Ala Gln Pro Ser Leu
                580                 585                 590

Thr Thr Thr Ser Arg Ser Pro Val Ser Pro Ala His Gln Ile Ser Val
            595                 600                 605

Pro Ala Ala Thr Gln Pro Ala Ala Leu Pro Thr Leu Leu Pro Ser Gln
        610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Pro Thr Ala Leu Gly
            660                 665                 670

Glu Ala Gly Leu Ala Glu His Ser Gln Arg Asp Asp Arg Trp Leu Leu
        675                 680                 685

Val Ala Leu Leu Val Pro Thr Cys Val Phe Leu Val Val Leu Leu Ala
690                 695                 700

Leu Gly Ile Val Tyr Cys Thr Arg Cys Gly His Ala Pro Asn Lys
                705                 710                 715                 720

Arg Ile Thr Asp Cys Tyr Arg Trp Val Ile His Ala Gly Ser Lys Ser
            725                 730                 735

Pro Thr Glu Pro Met Pro Pro Arg Gly Ser Leu Thr Gly Val Gln Thr
        740                 745                 750

Cys Arg Thr Ser Val
        755

<210> SEQ ID NO 4
<211> LENGTH: 661
<212> TYPE: PRT
<213> ORGANISM: Homo sapiens

<400> SEQUENCE: 4

Trp Ala Ala Glu Pro Arg Ala Ala Cys Gly Pro Ser Ser Cys Tyr Ala
1               5                   10                  15

Leu Phe Pro Arg Arg Arg Thr Phe Leu Glu Ala Trp Arg Ala Cys Arg
            20                  25                  30

Glu Leu Gly Gly Asp Leu Ala Thr Pro Arg Thr Pro Glu Glu Ala Gln
        35                  40                  45

Arg Val Asp Ser Leu Val Gly Ala Gly Pro Ala Ser Arg Leu Leu Trp
    50                  55                  60

Ile Gly Leu Gln Arg Gln Ala Arg Gln Cys Gln Leu Gln Arg Pro Leu
65                  70                  75                  80

Arg Gly Phe Thr Trp Thr Thr Gly Asp Gln Asp Thr Ala Phe Thr Asn
                85                  90                  95

Trp Ala Gln Pro Ala Ser Gly Gly Pro Cys Pro Ala Gln Arg Cys Val
            100                 105                 110

Ala Leu Glu Ala Ser Gly Glu His Arg Trp Leu Glu Gly Ser Cys Thr
        115                 120                 125

Leu Ala Val Asp Gly Tyr Leu Cys Gln Phe Gly Phe Glu Gly Ala Cys
    130                 135                 140

Pro Ala Leu Gln Asp Glu Ala Gly Gln Ala Gly Pro Ala Val Tyr Thr
145                 150                 155                 160

Thr Pro Phe His Leu Val Ser Thr Glu Phe Glu Trp Leu Pro Phe Gly
                165                 170                 175

Ser Val Ala Ala Val Gln Cys Gln Ala Gly Arg Gly Ala Ser Leu Leu
            180                 185                 190
```

```
Cys Val Lys Gln Pro Glu Gly Val Gly Trp Ser Arg Ala Gly Pro
        195                 200                 205
Leu Cys Leu Gly Thr Gly Cys Ser Pro Asp Asn Gly Gly Cys Glu His
    210                 215                 220
Glu Cys Val Glu Glu Val Asp Gly His Val Ser Cys Arg Cys Thr Glu
225                 230                 235                 240
Gly Phe Arg Leu Ala Ala Asp Gly Arg Ser Cys Glu Asp Pro Cys Ala
                245                 250                 255
Gln Ala Pro Cys Glu Gln Gln Cys Glu Pro Gly Gly Pro Gln Gly Tyr
                260                 265                 270
Ser Cys His Cys Arg Leu Gly Phe Arg Pro Ala Glu Asp Pro His
        275                 280                 285
Arg Cys Val Asp Thr Asp Glu Cys Gln Ile Ala Gly Val Cys Gln Gln
    290                 295                 300
Met Cys Val Asn Tyr Val Gly Gly Phe Glu Cys Tyr Cys Ser Glu Gly
305                 310                 315                 320
His Glu Leu Glu Ala Asp Gly Ile Ser Cys Ser Pro Ala Gly Ala Met
                325                 330                 335
Gly Ala Gln Ala Ser Gln Asp Leu Gly Asp Glu Leu Leu Asp Asp Gly
                340                 345                 350
Glu Asp Glu Glu Asp Glu Asp Glu Ala Trp Lys Ala Phe Asn Gly Gly
                355                 360                 365
Trp Thr Glu Met Pro Gly Ile Leu Trp Met Glu Pro Thr Gln Pro Pro
        370                 375                 380
Asp Phe Ala Leu Ala Tyr Arg Pro Ser Phe Pro Glu Asp Arg Glu Pro
385                 390                 395                 400
Gln Ile Pro Tyr Pro Glu Pro Thr Trp Pro Pro Pro Leu Ser Ala Pro
                405                 410                 415
Arg Val Pro Tyr His Ser Ser Val Leu Ser Val Thr Arg Pro Val Val
                420                 425                 430
Val Ser Ala Thr His Pro Thr Leu Pro Ser Ala His Gln Pro Pro Val
        435                 440                 445
Ile Pro Ala Thr His Pro Ala Leu Ser Arg Asp His Gln Ile Pro Val
    450                 455                 460
Ile Ala Ala Asn Tyr Pro Asp Leu Pro Ser Ala Tyr Gln Pro Gly Ile
465                 470                 475                 480
Leu Ser Val Ser His Ser Ala Gln Pro Pro Ala His Gln Pro Pro Met
                485                 490                 495
Ile Ser Thr Lys Tyr Pro Glu Leu Phe Pro Ala His Gln Ser Pro Met
                500                 505                 510
Phe Pro Asp Thr Arg Val Ala Gly Thr Gln Thr Thr Thr His Leu Pro
        515                 520                 525
Gly Ile Pro Pro Asn His Ala Pro Leu Val Thr Thr Leu Gly Ala Gln
    530                 535                 540
Leu Pro Pro Gln Ala Pro Asp Ala Leu Val Leu Arg Thr Gln Ala Thr
545                 550                 555                 560
Gln Leu Pro Ile Ile Pro Thr Ala Gln Pro Ser Leu Thr Thr Thr Ser
                565                 570                 575
Arg Ser Pro Val Ser Pro Ala His Gln Ile Ser Val Pro Ala Ala Thr
                580                 585                 590
Gln Pro Ala Ala Leu Pro Thr Leu Leu Pro Ser Gln Ser Pro Thr Asn
                595                 600                 605
```

-continued

```
Gln Thr Ser Pro Ile Ser Pro Thr His Pro His Ser Lys Ala Pro Gln
    610             615             620

Ile Pro Arg Glu Asp Gly Pro Ser Pro Lys Leu Ala Leu Trp Leu Pro
625             630             635             640

Ser Pro Ala Pro Thr Ala Ala Pro Thr Ala Leu Gly Glu Ala Gly Leu
            645             650             655

Ala Glu His Ser Gln
            660
```